(12) United States Patent
Romero Ugalde et al.

(10) Patent No.: US 12,383,672 B2
(45) Date of Patent: Aug. 12, 2025

(54) AUTOMATED SYSTEM FOR CONTROLLING THE BLOOD SUGAR OF A PATIENT

(71) Applicant: Commissariat à l'Énergie Atomique et aux Énergies Alternatives, Paris (FR)

(72) Inventors: Hector-Manuel Romero Ugalde, Grenoble (FR); Eléonore Maeva Doron, Grenoble (FR); Stéphane Bonnet, Grenoble (FR); Romain Blanc, Grenoble (FR); Chantal Simon, Lyons (FR); Mael Garnotel, Pierre-Benite (FR)

(73) Assignee: Commissariat à l'Énergie Atomique et aux Énergies Alternatives, Paris (FR)

( * ) Notice: Subject to any disclaimer, the term of this patent is extended or adjusted under 35 U.S.C. 154(b) by 1143 days.

(21) Appl. No.: 17/255,485

(22) PCT Filed: Jun. 27, 2019

(86) PCT No.: PCT/FR2019/051598
§ 371 (c)(1),
(2) Date: Dec. 23, 2020

(87) PCT Pub. No.: WO2020/002848
PCT Pub. Date: Jan. 2, 2020

(65) Prior Publication Data
US 2021/0275743 A1 Sep. 9, 2021

(30) Foreign Application Priority Data
Jun. 29, 2018 (FR) ...................................... 1856016

(51) Int. Cl.
*G16H 20/17* (2018.01)
*A61M 5/172* (2006.01)
*G16H 50/50* (2018.01)

(52) U.S. Cl.
CPC .......... *A61M 5/1723* (2013.01); *G16H 20/17* (2018.01); *G16H 50/50* (2018.01); *A61M 2005/1726* (2013.01); *A61M 2205/702* (2013.01); *A61M 2230/04* (2013.01); *A61M 2230/201* (2013.01); *A61M 2230/63* (2013.01)

(58) Field of Classification Search
CPC ................ A61B 5/14532; A61B 5/157; A61B 2560/0223; A61B 5/4839; A61B 5/7275; A61B 5/7278; A61B 5/7282; A61B 5/7239; A61B 5/7235; A61B 5/7207; A61B 5/721; A61B 5/7264; A61B 5/7271; A61B 5/024; A61B 5/02405; A61B 5/02438; A61B 5/02444; A61B 5/0255; A61B 5/72; A61B 5/02; A61B 5/0205; A61B 5/021; A61B 5/02416; A61M 2230/201; A61M 2230/00; A61M 2230/005; A61M 2230/04; A61M 2230/60; A61M 2230/63; A61M 2210/125; A61M 2210/12; G16H 50/20; G16H 40/63; G16H 40/40; G16H 10/40; G16H 40/67; G16H 50/50; G16H 10/60; G16H 50/30; G16H 50/70; G16H 20/10; G16H 15/00; G16H 70/20; G16H 20/17; G16H 40/60; G16H 50/00; G16H 70/60; G01N 27/3271; G01N 33/66; G01N 33/49; G01N 33/492; A61P 3/08; A61P 3/10; C12Q 1/006; C12Q 1/54; C12Q 1/025; G16B 5/00
See application file for complete search history.

(56) References Cited

U.S. PATENT DOCUMENTS

| | | | |
|---|---|---|---|
| 6,923,763 B1* | 8/2005 | Kovatchev | G16H 20/17 128/920 |
| 11,484,652 B2* | 11/2022 | Rousson | A61M 5/1723 |
| 11,883,162 B2* | 1/2024 | Romero Ugalde | A61M 5/1723 |
| 2010/0057043 A1* | 3/2010 | Kovatchev | G16H 20/17 600/301 |
| 2016/0354543 A1 | 12/2016 | Cinar et al. | |
| 2021/0275743 A1* | 9/2021 | Romero Ugalde | A61B 5/14532 |

FOREIGN PATENT DOCUMENTS

FR 3 056 095 A1 3/2018

OTHER PUBLICATIONS

Hovorka, R. Nonlinear model predictive control of glucose concentration in subjects with type 1 diabetes (2004) Physiological Measurement vol. 25, p. 905-920. (Year: 2004).*
Mansell, E. Shedding light on grey noise in diabetes modelling. (2017) Biomedical Signal Processing and Control. vol. 31, p. 16-30. (Year: 2017).*
International Preliminary Report on Patentability for International Application No. PCT/FR2019/051598, mailed Jan. 7, 2021.
International Search Report and Written Opinion for International Application No. PCT/FR2019/051598, mailed Dec. 6, 2019.
Roy et al., Dynamic modeling of exercise effects on plasma glucose and insulin levels. Journal of Diabetes Science and Technology. May 1, 2007;1(3):338-47.

* cited by examiner

*Primary Examiner* — Mary K Zeman
(74) *Attorney, Agent, or Firm* — Wolf, Greenfield & Sacks, P.C.

(57) ABSTRACT

An automated system for controlling a patient's blood glucose, including a processing and control unit configured to predict the future trend of the patient's blood glucose based on a physiological model, wherein the physiological model includes a differential equation system describing the time variation of a plurality of state variables, and wherein at least one of the equations of the system takes as an input a variable EE(t) representative of the time variation of the patient's energy expenditure.

7 Claims, 3 Drawing Sheets

AUTOMATED SYSTEM FOR CONTROLLING THE BLOOD SUGAR OF A PATIENT

This application is a national stage filing under 35 U.S.C. § 371 of International Patent Application Serial No. PCT/FR2019/051598, filed Jun. 27, 2019, which claims priority to French patent application FR18/56016. The contents of these applications are incorporated herein by reference in their entireties.

BACKGROUND

The present disclosure concerns the field of automated blood glucose control systems, and more particularly aims at a control system capable of predicting the future trend of a patient's blood glucose.

DISCUSSION OF THE RELATED ART

Automated blood glucose regulation systems, also called artificial pancreases, enabling to automatically regulate the insulin inputs of a diabetic patient based on his/her blood glucose history, on his/her meal history, on his/her insulin injection history have already been provided, for example, in international patent application No. WO2018055283 (B15018/DD16959), in international patent application No. WO2018055284 (B15267/DD17175), and in French patent application No. 1756960 (B15860/DD18587LP) filed on Jul. 21, 2017.

The regulation systems described in the above-mentioned patent applications are MPC-type (model-based predictive control) systems, also called predictive control systems, where the regulation of the administered insulin dose takes into account a prediction of the future trend of the patient's blood glucose, obtained from a mathematical model. More particularly, in the systems described in the above-mentioned patent applications, the model used to predict the future trend of the patient's blood glucose is a physiological model describing the assimilation of insulin by the patient's body and its impact on the patient's blood glucose.

More generally, many automated blood glucose control applications use physiological models to predict the future trend of a patient's blood glucose, and implement, taking the prediction into account, actions aiming at maintaining the patient's blood glucose within a desired range.

Known physiological models for predicting the future trend of a patient's blood glucose however have limitations. In particular, in certain conditions, the predictions performed by known physiological models may sometimes not be reliable. This may result in errors in the control or the regulation of the patient's blood glucose, which may cause risks for the patient.

SUMMARY

Thus, an embodiment provides an automated system for controlling a patient's blood glucose, comprising a processing and control unit configured to predict the future trend of the patient's blood glucose based on a physiological model, wherein the physiological model comprises a differential equation system describing the time variation of a plurality of state variables, and wherein at least one of the equations of the system takes as an input a variable EE(t) representative of the time variation of the patient's energy expenditure.

According to an embodiment, the system comprises a device for measuring a physical activity of the patient, the input variable EE(t) of the model being calculated by the processing and control unit from output data PA (t) of the measurement device.

According to an embodiment, the measurement device comprises a sensor of the patient's motions.

According to an embodiment, the measurement device further comprises a sensor of the patient's heart rate.

According to an embodiment, the motion sensor delivers a signal $S_{CPM}$ representative of motions performed by the patient, and the heart beat sensor delivers a signal $S_{HR}$ representative of the patient's heart rate, and wherein the input variable EE(t) of the model is calculated as follows by the processing and control unit:

$$EE(t) = \begin{cases} \alpha_1 * S_{HR}(t) + \beta_1, & S_{HR} \geq S1 \\ \alpha_2 * S_{LC}(t) + \beta_2, & S_{HR} < S1 \text{ et } S_{LC} < S2 \\ \alpha_3 * S_{LC}(t) + \beta_3, & S_{HR} < S1 \text{ et } S_{LC} \geq S2 \end{cases}$$

where signal $S_{LC}$ is a linear combination of signals $S_{HR}$ and $S_{CMP}$, and where quantities $\alpha_1$, $\alpha_2$, $\alpha_3$, $\beta_1$, $\beta_2$, $\beta_3$, S1, and S2 are parameters of the system.

According to an embodiment, the physiological model further takes as inputs a variable i(t) representative of the time variation of the quantity of insulin injected to the patient, and a variable cho(t) representative of the time variation of the quantity of carbohydrates ingested by the patient.

According to an embodiment, the system further comprises a blood glucose sensor.

According to an embodiment, the processing and control unit is capable of implementing a step of automatic calibration of the physiological model comprising a step of estimation of a set of parameters of the differential equation system by minimization of a quantity m representative of the error, during a past observation period, between the blood glucose estimated based on the physiological model and the blood glucose measured by the sensor.

According to an embodiment, the quantity is defined as follows:

$$m = \frac{1}{\Delta T} \sum_{t=t_0}^{t_0+\Delta T} |G'(t) - G(t)|^2$$

where t is a discretized time variable, $t_0$ is the time of beginning of the past observation period, and $t_0+\Delta T$ is the time of end of the past observation period.

According to an embodiment, the system further comprises an insulin injection device, wherein the processing and control unit is capable of controlling the insulin injection device taking into account the prediction of the future trend of the patient's blood glucose made based on the physiological model.

According to an embodiment, the equation comprises a term $-(K_{EE}*EE(t))$ representative of a glucose consumption by the muscles, where $k_{EE}$ is a parameter of the physiological model.

According to an embodiment, the equation is defined as follows:

$$\frac{dQ_2}{dt} = x_1(t) \cdot Q_1(t) - [k_{12} + x_2(t)] \cdot Q_2(t) - k_{EE} \cdot EE(t)$$

where $Q_1$ and $Q_2$ are state variables respectively corresponding to glucose masses in first and second compartments, where $x_1$ and $x_2$ are state variables, each standing for an action of insulin on the kinetics of glucose, and where $k_{12}$ is a parameter of the physiological model.

BRIEF DESCRIPTION OF THE DRAWINGS

The foregoing and other features and advantages will be discussed in detail in the following non-limiting description of specific embodiments in connection with the accompanying drawings, in which.

DETAILED DESCRIPTION

Like features have been designated by like references in the various figures. For clarity, only those elements which are useful to the understanding of the described embodiments have been shown and are detailed. In particular, the blood glucose measurement devices and the insulin injection devices of the described regulation systems have not been detailed, the described embodiments being compatible with all or most of known blood glucose measurement and insulin injection devices. Further, the hardware implementation of the processing and control unit of the described regulation systems has not been detailed, the forming of such a processing and control unit being within the abilities of those skilled in the art based on the functional indications of the present disclosure. Unless specified otherwise, the expressions "approximately", "substantially", "around", and "in the order of" signify within 10% and, preferably, within 5%.

Figure 1:
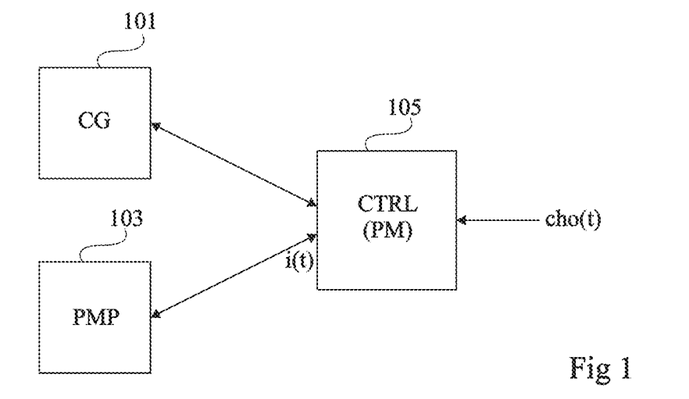
FIG. 1 schematically shows in the form of blocks an example of an automated system for regulating a patient's blood glucose.

FIG. 1 schematically shows in the form of blocks an example of an automated system for regulating a patient's blood glucose of the type described in the above-mentioned international patent applications WO2018055283 and WO2018055284, and French patent application No. 1756960.

The system of FIG. 1 comprises a sensor 101 (CG) capable of measuring the patient's blood glucose. In normal operation, sensor 101 may be permanently positioned on or inside of the patient's body, for example, at the level of his/her abdomen. Sensor 101 is for example a CGM-type ("Continuous Glucose Monitoring") sensor, that is, a sensor capable of continuously measuring (for example, at least once every five minutes) the patient's blood glucose. Sensor 101 is for example a subcutaneous blood glucose sensor.

The system of FIG. 1 further comprises an insulin injection device 103 (PMP), for example, a subcutaneous injection device. Device 103 is for example, an automatic injection device of insulin pump type, comprising an insulin reservoir connected to an injection needle implanted under the patient's skin, and the pump may be electrically controlled to automatically inject determined insulin doses at determined times. In normal operation, injection device 103 may be permanently positioned inside of or on the patient's body, for example, at the level of his/her abdomen.

The system of FIG. 1 further comprises a processing and control unit 105 (CTRL (PM)) connected on the one hand to blood glucose sensor 101, for example, by a wire link or by a radio (wireless) link, and on the other hand to injection device 103, for example, by wire or radio link. In operation, processing and control unit 105 is capable of receiving the data relative to the patient's blood glucose measured by sensor 101, and of electrically controlling device 103 to inject to the patient determined insulin doses at determined times. In this example, processing and control unit 105 is further capable of receiving, via a user interface, not detailed, data cho(t) representative of the time variation of the quantity of glucose ingested by the patient.

Processing and control unit 105 is capable of determining the insulin doses to be injected to the patient by taking into account, in particular, the history of the blood glucose measured by sensor 101, the history of the insulin injected by device 103, and the history of carbohydrate ingestion by the patient. To achieve this, processing and control unit 105 comprises a digital calculation circuit (not detailed), for example comprising a microprocessor. Processing and control unit 105 is for example a mobile device carried by the patient all along the day and/or the night, for example, a smartphone-type device configured to implement a regulation method of the type described hereafter.

In the example of FIG. 1, processing and control unit 105 is capable of determining the quantity of insulin to be administered to the patient, taking into account a prediction of the future trend of his/her blood glucose over time. More particularly, processing and control unit 105 is capable, based on the injected insulin history and on the ingested carbohydrate history, and based on a physiological model describing the assimilation of insulin by the patient's body and its impact on blood glucose, of determining a curve representative of the expected trend of the patient's blood glucose over time, over a period to come called prediction period or prediction horizon, for example, a period from 1 to 10 hours. Taking this curve into account, processing and control unit 105 determines the insulin doses that should be injected to the patient during the prediction period to come, so that the patient's real blood glucose (as opposed to the blood glucose estimated based on the physiological model) remains within acceptable limits, and in particular to limit risks of hyperglycemia or of hypoglycemia. In such an operating mode, as will be explained in further detail hereafter, the data relative to the real blood glucose measured by sensor 101 are mainly used for purposes of calibration of the physiological model.

Figure 2:
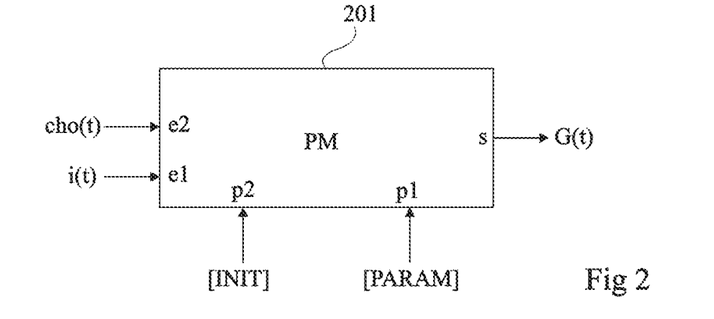
FIG. 2 is a simplified representation of a physiological model used in the system of FIG. 1 to predict the future trend of the patient's blood glucose.

FIG. 2 is a simplified representation of a physiological model 201 (PM) used in the system of FIG. 1 to predict the future trend of the patient's blood glucose. In FIG. 2, the model is shown in the form of a processing block comprising:

an input e1 having a signal i(t) representative of the variation, over time t, of the quantity of insulin injected to the patient, applied thereto;

an input e2 having a signal cho(t) representative of the trend, over time t, of the quantity of glucose ingested by the patient, applied thereto; and an output s delivering a signal G(t) representative of the trend, over time t, of the patient's blood glucose.

Physiological model 201 is for example a compartmental model comprising, in addition to input variables i(t) and cho(t) and output variable G(t), a plurality of state variables corresponding to physiological variables of the patient, varying over time. The time variation of the state variables and of output variable G(t) is ruled by a differential equation system comprising a plurality of parameters represented in FIG. 2 by a vector [PARAM] applied to an input p1 of block 201. The response of the physiological model is further conditioned by the initial states or initial values assigned to the state variables, represented in FIG. 2 by a vector [INIT] applied to an input p2 of block 201.

Figure 3:
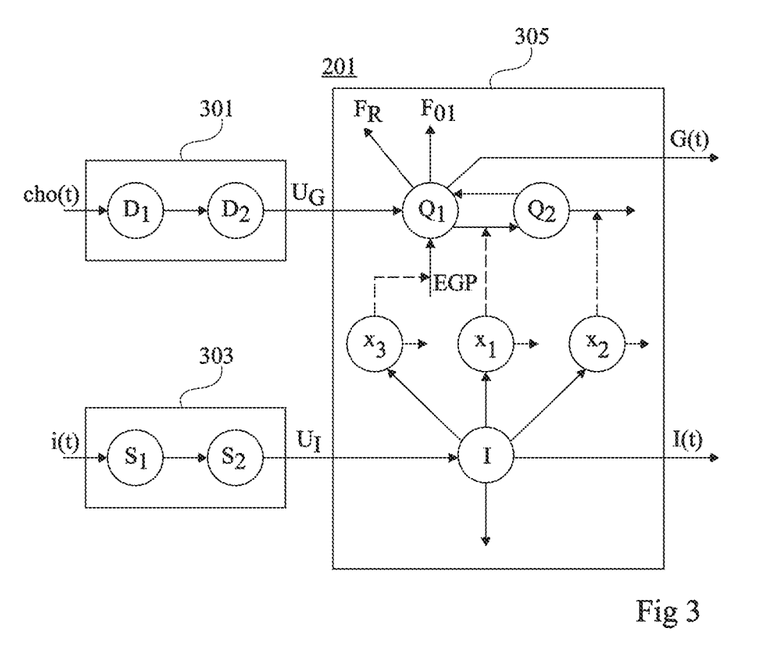
FIG. 3 is a diagram showing in further detail an embodiment of the physiological model of FIG. 2.

FIG. 3 is a diagram showing in further detail an example of the physiological model 201 used in the system of FIG. 1 to predict the future trend of the patient's blood glucose. This example of model, known as the Hovorka model, is described in further detail in the article entitled "Nonlinear model predictive control of glucose concentration in subjects with type 1 diabetes" of Roman Hovorka et al. (Physiol Meas. 2004; 25:905-920), and in the article entitled "Partitioning glucose distribution/transport, disposal, and endogenous production during IVGTT", of Roman Hovorka et al. (Am J Physiol Endocrinol Metab 282: E992-E1007, 2002).

The physiological model of FIG. 3 comprises a first bicompartmental sub-model 301 describing the effect of a dietary intake of carbohydrates on the rate of occurrence of glucose in the blood plasma. Sub-model 301 takes as an input the quantity of ingested carbohydrates cho(t), for example, in mmol/min, and outputs a rate $U_G$ of glucose absorption in the blood plasma, for example, in mmol/min. Sub-model 301 comprises two state variables $D_1$ and $D_2$ respectively corresponding to masses of glucose, for example, in mmol, in first and second compartments.

The model of FIG. 3 further comprises a second bicompartmental sub-model 303 describing the absorption, in the blood plasma, of the insulin administered to the patient. Sub-model 303 takes as an input quantity of insulin i(t) injected to the patient, for example, in mU/min (where U designates an international insulin unit, that is, the biological equivalent of approximately 0.0347 of human insulin), and outputs a rate $U_I$ of insulin absorption in the blood plasma, for example, in mU/min. Sub-model 303 comprises two state variables $S_1$ and $S_2$ respectively corresponding to insulin masses, for example, in mmol, in first and second compartments.

The model of FIG. 3 further comprises a third sub-model 305 describing the glucose regulation by the patient's body. Sub-model 305 takes as inputs the absorption rates $U_G$ of carbohydrates and $U_I$ of insulin, and output the blood glucose G(t), that is, the glucose concentration in the blood plasma, for example in mmol/l. Sub-model 305 comprises six state variables $Q_1$, $Q_2$, $x_3$, $x_1$, $x_2$, I. Variables Q1 and Q2 respectively correspond to glucose masses, for example, in mmol, in first and second compartments. Variables $x_1$, $x_2$, $x_3$ are unit-less variables representing each of the actions of insulin on the kinetics of glucose. Variable I corresponds to the insulinemia, that is, the insulin concentration in the blood plasma, for example, in mU/l. It should be noted that in the example of FIG. 3, an output delivering a signal I (t) representative of the time variation of variable I has been shown. This output is however optional.

The Hovorka model is ruled by the following equation system:

$$G(t) = \frac{Q_1(t)}{V_G} \quad \text{(eq1)}$$

$$\frac{dQ_1}{dt} = \quad \text{(eq2)}$$
$$-\left[\frac{F_{01}^c}{V_G \cdot G(t)} + x_1(t)\right] \cdot Q_1(t) + k_{12}Q_2(t) - F_R + EGP_0 \cdot [1 - x_3(t)] + U_G(t)$$

$$\frac{dQ_2}{dt} = x_1(t) \cdot Q_1(t) - [k_{12} + x_2(t)] \cdot Q_2(t) \quad \text{(eq3)}$$

$$\frac{dx_1}{dt} = -k_{b1} \cdot x_1(t) + k_{a1} \cdot I(t) \quad \text{(eq4)}$$

$$\frac{dx_2}{dt} = -k_{b2} \cdot x_2(t) + k_{a2} \cdot I(t) \quad \text{(eq5)}$$

$$\frac{dx_3}{dt} = -k_{b3} \cdot x_3(t) + k_{a3} \cdot I(t) \quad \text{(eq6)}$$

$$\frac{dS_1}{dt} = i(t) - k_a \cdot S_1(t) \quad \text{(eq7)}$$

$$\frac{dS_2}{dt} = k_a \cdot S_1(t) - k_a \cdot S_2(t) \quad \text{(eq8)}$$

$$\frac{dI}{dt} = \frac{k_a \cdot S_2(t)}{V_I} - k_e \cdot I(t) \quad \text{(eq9)}$$

$$\frac{dD_1}{dt} = cho(t) - \frac{D_1(t)}{t_{max}} \quad \text{(eq10)}$$

$$\frac{dD_2}{dt} = \frac{D_1(t)}{t_{max}} - \frac{D_2(t)}{t_{max}} \quad \text{(eq11)}$$

$$U_G = \frac{D_2(t)}{t_{max}} \quad \text{(eq12)}$$

Avec:

$$F_{01}^c = \frac{F_{01} \cdot G(t)}{0.85 \cdot (G(t) + 1.0)} \quad \text{(eq13)}$$

$$F_R = \begin{cases} R(G-9) \cdot V_G & \text{if } G > 9 \\ 0 & \text{otherwise} \end{cases} \quad \text{(eq14)}$$

In this equation system, quantities $V_G$, $F_{01}$, $k_{12}$, $F_R$, $EGP_0$, $k_{b1}$, $k_{a1}$, $k_{b2}$, $k_{a2}$, $k_{b3}$, $k_{a3}$, $k_a$, $V_I$, $k_e$, and $t_{max}$ are parameters. $V_G$ corresponds to the glucose distribution volume, for example, in liter, $F_{01}$ corresponds to a transfer rate of the non-insulin-dependent glucose, for example, in mmol/min, $k_{12}$ corresponds to a constant of the transfer rate between the two compartments of sub-model 305, for example, in min$^{-1}$, $k_{a1}$, $k_{a2}$, $k_{a3}$ correspond to insulin deactivation rate constants, for example, in min$^{-1}$, $F_R$ corresponds to a glucose urination, for example, in mmol/min, $EGP_0$ corresponds to an endogenous production of glucose, for example, in min$^{-1}$, $k_{b1}$, $k_{b2}$, and $k_{b3}$ correspond to insulin activation rate constants, for example, in min$^{-1}$, $k_a$ corresponds to a subcutaneously injected insulin absorption rate constant, for example, in min$^{-1}$, $V_I$ corresponds to the insulin distribution volume, for example, in liters, $k_e$ corresponds to a rate of elimination of the plasma's insulin, for example, in min$^{-1}$, and $t_{max}$ corresponds to the time elapsed until the absorption peak of the glucose ingested by the patient, for example, in min. These fifteen parameters correspond to vector [PARAM] of the representation of FIG. 2. Vector [INIT] comprises ten values corresponding to the initial values (at a time $t_0$ of beginning of a phase of simulation of the patient's behavior based on the model) assigned to the ten state variables $D_1$, $D_2$, $S_1$, $S_2$, $Q_1$, $Q_2$, $x_1$, $x_2$, $x_3$, and I of the model.

Among the parameters of vector [PARAM], some may be considered as constant for a given patient. These are for example parameters $k_{12}$, $k_{a1}$, $k_{a2}$, $k_{a3}$, $k_a$, $k_e$, $V_I$, $V_G$, and $t_{max}$. Other parameters, called time-dependent parameters hereafter, are however capable of varying over time, for example, parameters $k_{b1}$, $k_{b2}$, $k_{b3}$, $EGP_0$, $F_{01}$, and $F_R$. Due to the variability of certain parameters of the system, it is in practice necessary to regularly recalibrate the model used, for example, every 1 to 20 minutes, for example, every 5 minutes, to make sure that the predictions of the model remain relevant. Such an update of the model, called model personalization, should be capable of being automatically carried out by the system of FIG. 1, that is, without requiring physically measuring the time-dependent parameters of the system from the patient, and then transmitting them to processing and control unit 105.

Figure 4:
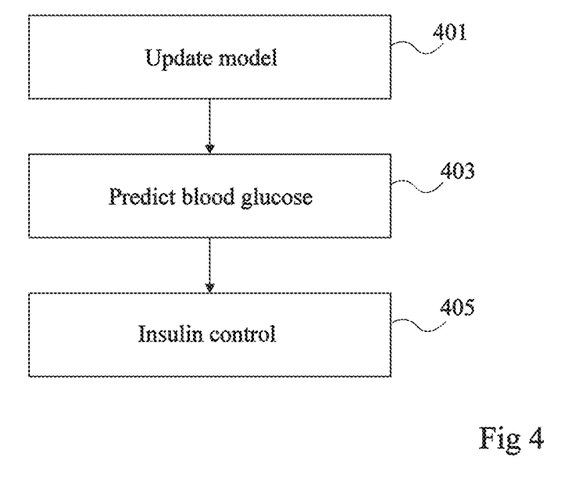
FIG. 4 is a diagram illustrating an example of an automated blood glucose regulation method capable of being implemented by the system of FIG. 1.

FIG. 4 is a diagram illustrating an example of an automated blood glucose regulation method implemented by the system of FIG. 1.

This method comprises a step 401 of recalibration or update of the model, which may for example be repeated at regular intervals, for example, every 1 to 20 minutes. During this step, processing and control unit 105 implements a method of re-estimation of the time-dependent parameters of the model, taking into account the data relative to the insulin effectively injected by device 103 and the data relative to the real blood glucose measured by sensor 101 for a past observation period of duration ΔT, for example a period from 1 to 10 hours preceding the calibration step. More particularly, during the calibration step, processing and control unit 105 simulates the patient's behavior over the past observation period based on the physiological model (taking into account possible carbohydrate ingestions and insulin injections during this period) and compares the curve of the blood glucose G(t) estimated by the model with the curve of the real blood glucose $G^r(t)$ measured by the sensor during this same period. Processing and control unit 105 then searches, for the time-dependent parameters of the model, a set of values leading to minimizing a quantity representative of the error between the blood glucose curve estimated by the model and the real blood glucose curve measured by the sensor during the observation period.

As an example, the processing and control unit searches for a set of parameters leading to minimizing an indicator m representative of the mean standard deviation between the estimated blood glucose G(t) and the real blood glucose $G^r(t)$, for example defined as follows:

$$m = \frac{1}{\Delta T} \sum_{t=t_0}^{t_0+\Delta T} |G^r(t) - G(t)|^2 \tag{eq15}$$

where t is the discretized time variable, $t_0$ corresponds to the time of beginning of the past observation phase, $t_0+T$ corresponds to the end time of the past observation phase (for example corresponding to the time of beginning of the model calibration step), $G^r$ is the curve of time variation of the real blood glucose measured by sensor 101 during period [t0, $t_0+\Delta T$], and G is the curve of the blood glucose estimated based on the model during period [$t_0$, $t_0+\Delta T$]. The optimal parameter search algorithm used during this step is not detailed in the present application, the described embodiments being compatible with usual algorithms used in various fields to solve problems of parameter optimization by minimization of a cost function.

It should be noted that during step 401, in addition to the time-dependent parameters of the model, processing and control unit 105 defines a vector [INIT] of initial states (states at time $t_0-\Delta T$) of the state variables of the model, to be able to simulate the patient's behavior from the model. To define the initial states of the state variables of the model, a first possibility comprises making the assumption that, in the period preceding the observation period [$t_0-\Delta T$, $t_0$] having the model calibration based thereon, the patient was in a stationary state, with a constant flow of injected insulin, and no dietary intake of carbohydrates. Under this assumption, all the derivatives of the differential equation system may be considered as zero at initial time $t_0-\Delta T$. The values at time $t_0-\Delta T$ of the state variables of the system may then be analytically calculated. To improve the initialization, another possibility comprises making the same assumptions as previously, but adding the constraint that the glucose estimated at time $t_0-\Delta T$ is equal to the real glucose measured by the sensor. To further improve the initialization, another possibility is to consider the initial states of the state variables of the model as random variables, just as the time-dependent parameters of the model. The initial states of the state variables are then determined in the same way as the time-dependent parameters of the model, that is, processing and control unit 105 searches for a set of values of initial states [INIT] resulting in minimizing a quantity representative of the error between the curve of the blood glucose estimated by the model and the curve of the real blood glucose during the past observation period.

The method of FIG. 4 further comprises, after step 401, a step 403 of prediction, by processing and control unit 105, of the time variation of the patient's blood glucose over a period to come [t0, $t_0+T_{pred}$] of duration $T_{pred}$, for example, in the range from 1 to 10 hours, based on the physiological model updated at step 401 and taking into account the history of the insulin injected to the patient and the history of carbohydrates ingested by the patient.

The method of FIG. 4 further comprises, after step 403, a step 405 of determination, by processing and control unit 105, taking into account the curve of the future blood glucose predicted at step 403, of insulin doses to be injected to the patient for a period [t0, $t_0+T_{pred}$] to come. At the end of this step, processing and control unit 105 may program injection device 103 to administer the doses determined during the prediction period [t0, $t_0+T_{pred}$] to come.

Steps 403 of prediction of the blood glucose and 405 of determination of the future doses of insulin to be administered may for example be repeated at each update of the physiological model (that is, after each iteration of step 401), for each new carbohydrate ingestion notified by the patient, and/or for each new administration of an insulin dose by injection device 103.

In a regulation system of the type described in relation with FIGS. 1 to 4, the reliability of the prediction of the future trend of the blood glucose is particularly important to correctly determine the insulin doses to be administered to the patient, and accordingly to correctly regulate the patient's blood glucose.

More generally, in many automated blood glucose control applications, the prediction of the future trend of the patient's blood glucose plays an important role to enable to maintain the blood glucose within a desired range (for example corresponding to a normoglycemia range).

A limitation of known physiological models for the prediction of the future trend of a patient's blood glucose is that they do not take into account the patient's physical activity, which however has significant effects on his/her blood glucose. Thus, it may occur, particularly during and/or around periods of physical activity of the patient, that the predictions made by these models are not reliable. This may result in errors in the control or the regulation of the patient's blood glucose, which may cause risks for the patient.

According to an aspect of the described embodiments, a system where the prediction of the future trend of the patient's blood glucose is made by means of a physiological model taking as inputs not only the quantity of insulin injected to the patient and the quantity of carbohydrates ingested by the patient, but also data representative of the patient's physical activity, is provided.

Figure 5:
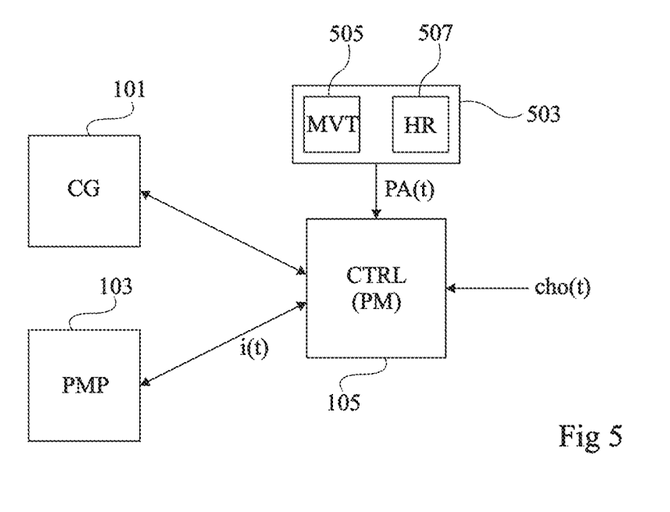
FIG. 5 schematically shows, in the form of blocks, an embodiment of an automated system for regulating a patient's blood glucose.

FIG. 5 schematically shows in the form of blocks an embodiment of an automated system for predicting a patient's blood glucose.

The system of FIG. 5 comprises the same elements as the system of FIG. 1, arranged substantially in the same way, and differs from the system of FIG. 1 essentially in that, in operation, processing and control unit 105 is capable of receiving data cho(t) representative of the time variation of the quantity of carbohydrates ingested by the patient and data i(t) representative of the time variation of the quantity of insulin injected to the patient, but also data PA (t) representative of the time variation of the patient's physical activity.

As in the example of FIG. 1, the ingested carbohydrate data cho(t) may for example be input by the patient via a user interface, not detailed.

The injected insulin data i(t) may also be input by the patient via a user interface. As a variant, the injected insulin data i(t) are directly communicated to processing and control unit 105 by insulin injection device 103. In the case where insulin injection device 103 is exclusively controlled by processing and control unit 105, the injected insulin data i(t) are known by processing and control unit 105 and do not need being transmitted thereto.

In the example of FIG. 5, the system comprises a device 503 capable of measuring the patient's physical activity. Device 503 is coupled to processing and control unit 105, for example, by a wire link or a radio link (wireless), and communicates to processing and control unit 105 the patient's physical activity data PA (t). Device 503 is for example a mobile device carried by the patient all along the day and/or the night. As an example, device 503 comprises at least one motion sensor 505 (MVT), for example, an accelerometer. Device 503 may further comprise a sensor 507 (HR) of the patient's heart rate.

In the embodiment of FIG. 5, processing and control unit 105 is configured to, based on a physiological model taking into account the injected insulin history, the ingested carbohydrate history, and the history of the patient's physical activity, determine a curve representative of the expected trend of the patient's blood glucose over time, over a period to come. Processing and control unit 105 may further be configured to, taking into account the curve of the predicted blood glucose, implement an action of control or of regulation of the patient's blood glucose to maintain the patient's blood glucose within a desired range, for example, similarly to what has been described in relation with FIGS. 1 to 4.

Figure 6:
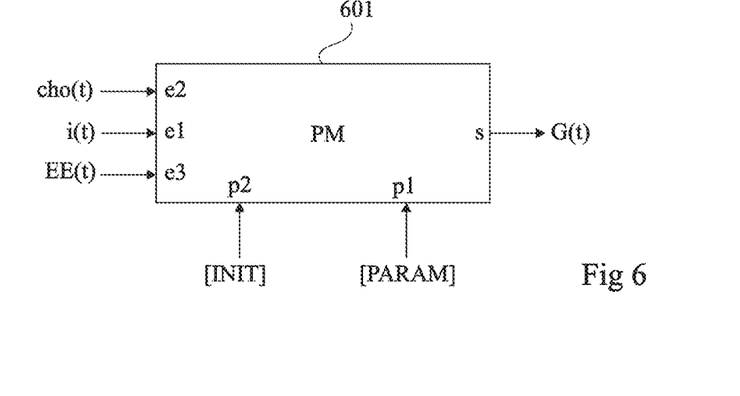
FIG. 6 is a simplified representation of a physiological model used in the system of FIG. 5 to predict the future trend of the patient's blood glucose.

FIG. 6 is a simplified representation of a physiological model 601 (PM) used in the system of FIG. 5 to predict the future trend of the patient's blood glucose. In FIG. 6, the model is shown in the form of a processing block comprising:

an input e1 having a signal i(t) representative of the variation, over time t, of the quantity of insulin injected to the patient, applied thereto;

an input e2 having a signal cho(t) representative of the trend, over time t, of the quantity of carbohydrates ingested by the patient, applied thereto;

an input e3 having a signal EE(t) representative of the time variation of the patient's energy expenditure, applied thereto; and an output s delivering a signal G(t) representative of the trend, over time t, of the patient's blood glucose.

As an example, signal EE(t) is representative of the quantity of energy spent at time t by the patient to enable his/her organism to operate properly, to ensure all its physical functions and, possibly, to make a physical effort.

The input variable EE(t) of the model may be calculated based on the output signals of motion sensor 505 and of heart rate sensor 507 of the system of FIG. 5. As an example, motion sensor 505 delivers a signal $S_{CPM}$ representative of the patient's motions, for example, representative of a number of motions per minute performed by the patient, for example, representative of the number of steps per minute performed by the patient, and heart rate sensor 507 outputs a signal representative of the patient's heart rate (number of pulses per minute). More particularly, in this example, signal $S_{HR}$ is equal to the difference between the patient's heart rate (number of beats per minute) at time t and the patient's heart rate at rest (which may be a constant of the system). Input variable EE(t) may then be calculated as follows:

$$EE(t) = \begin{cases} \alpha_1 * S_{HR}(t) + \beta_1, & S_{HR} \geq S1 \\ \alpha_2 * S_{LC}(t) + \beta_2, & S_{HR} < S1 \text{ et } S_{LC} < S2 \\ \alpha_3 * S_{LC}(t) + \beta_3, & S_{HR} < S1 \text{ et } S_{LC} \geq S2 \end{cases} \quad (eq16)$$

where signal $S_{LC}$ is a linear combination of signals $S_{HR}$ and $S_{CMP}$, such that $S_{LC}(t)=\theta 1*S_{CMP}(t)+\theta 2*S_{HR}(t)$, and quantities $\alpha_1$, $\alpha_2$, $\alpha_3$, $\beta_1$, $\beta_2$, $\beta_3$, $\theta 1$, $\theta 2$, S1, and S2 are parameters of the system. An example of a method of estimating an individual's energy expenditure, capable of being used to calculate input variable EE(t) of the model, is described in further detail in the article entitled "An original piecewise model for computing energy expenditure from accelerometer and heart rate signals" of H. M. Romero-Ugalde et al. (Physiological Measurement, vol. 38, no. 8, p. 1599, 2017).

Model 601 is a physiological model, that is, a mathematically model formed by an equation system modeling the different physiological mechanisms taking place in the patient's body and having an effect on his/her blood glucose. Model 601 is for example a compartmental model comprising, in addition to input variables i(t) and cho(t) and output variable G(t), a plurality of state variables corresponding to physiological variables of the patient, varying over time. Similarly to what has been described in relation with FIGS. 1 to 4, the time variation of the state variables and of output variable G(t) is ruled by a differential equation system comprising a plurality of parameters represented in FIG. 6 by a vector [PARAM] applied to an input p1 of block 601. The response of the physiological model is further conditioned by the initial states or initial values assigned to the state variables, represented in FIG. 2 by a vector [INIT] applied to an input p2 of block 601.

According to an aspect of an embodiment, physiological model 601 comprises at least one equation comprising a term $-(k_{EE}*EE(t))$, where $k_{EE}$ is a parameter of the model, for example, a constant parameter or a time-dependent parameter re-estimated at each update of the model (step 401 of the method of FIG. 4). Term $-(K_{EE}*EE(t))$ corresponds to a glucose sink representing the glucose consumption by the muscles, particularly during a physical activity. Term $-(K_{EE}*EE(t))$ is for example taken into account to calculate the time derivative of a variable of the model representative of a glucose mass in a compartment.

As an example, the physiological model 601 used in the system of FIG. 5 is a model based on the Hovorka model, capable of taking into account the patient's energy expenditure EE(t).

Figure 7:
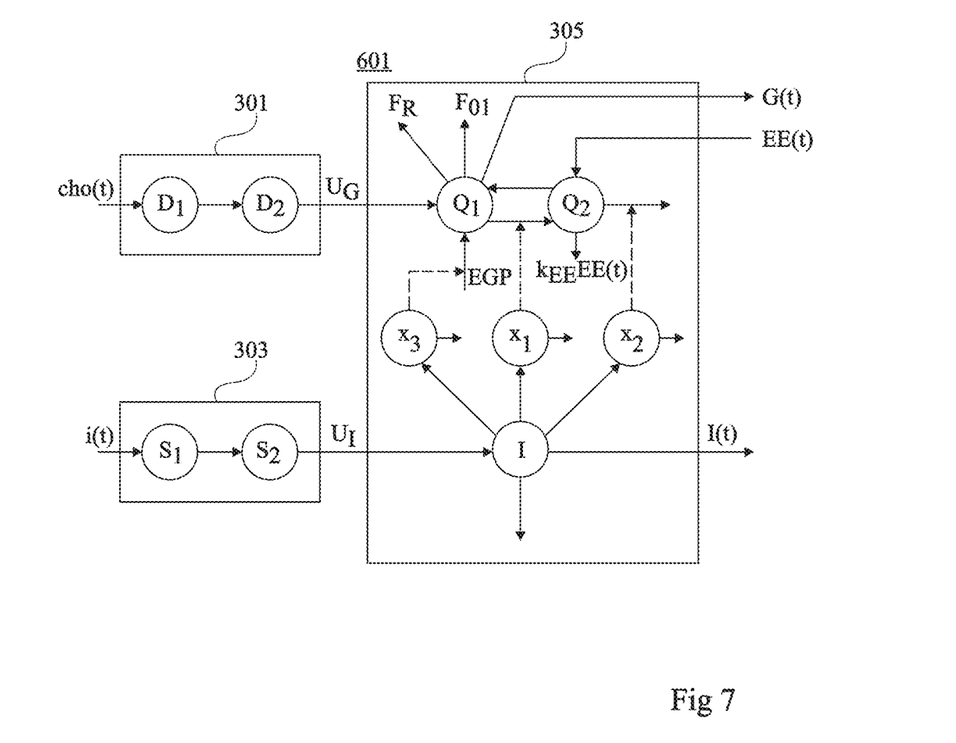
FIG. 7 is a diagram showing in further detail an embodiment of the physiological model of FIG. 6.

FIG. 7 is a diagram showing in further detail an example of the physiological model 601 used in the system of FIG. 5 to predict the future trend of the patient's blood glucose.

The physiological model of FIG. 7 is similar to the physiological model of FIG. 3 and differs from the model of FIG. 3 essentially in that, in the model of FIG. 7, sub-model 305, describing the regulation of glucose of the patient's body, takes as inputs not only the absorption rate $U_G$ of carbohydrates and $U_I$ of insulin, but also the patient's energy expenditure EE(t). More particularly, in the example of FIG. 7, the time variation of state variable Q2 depends on term $-(k_{EE}*EE(t))$. In this example, term $k_{EE}*EE(t)$, corresponding to a quantity of glucose consumed by the muscles according to the energy expenditure EE(t), is subtracted from the glucose quantity Q2 of the model.

The equation system ruling the model of FIG. 7 is for example identical to the system described in relation with FIG. 3, with the difference that, in the system of FIG. 7, equation eq3 of the system of FIG. 3 is replaced with the following equation eq3':

$$\frac{dQ_2}{dt} = x_1(t) \cdot Q_1(t) - [k_{12} + x_2(t)] \cdot Q_2(t) - k_{EE} \cdot EE(t) \quad (eq3')$$

As in the example of FIG. 3, FIG. 7 shows an output delivering a signal I (t) representative of the time variation of variable I. This output is however optional.

As an example, the system of FIG. 5 may be configured to implement an automated blood glucose regulation method identical or similar to the method described in relation with FIG. 4, based on the physiological model 601 described in relation with FIGS. 6 and 7 to replace the model 201 described in relation with FIGS. 2 and 3.

In this case, during step 401 of recalibration or update of the model, processing and control unit 105 takes into account, to re-estimate the time-dependent parameters of the model, not only the data relative to the insulin effectively injected by device 103 and the data relative to the real blood glucose measured by sensor 101 for a past observation period ΔT, but also data relative to the patient's energy expenditure over the past observation period ΔT, determined by means of physical activity measurement device 503.

During step 403, processing and control unit 105 predicts the time variation of the patient's blood glucose over a period to come [t0, $t_0+T_{pred}$] of duration $T_{pred}$, based on the physiological model updated at step 401 and taking into account the history of the insulin injected to the patient, the history of carbohydrates ingested by the patient, and the history of the patient's energy expenditure.

During step 405, processing and control unit 105 determines, taking into account the curve of the future blood glucose predicted at step 403, insulin doses to be injected to the patient the during period [t0, $t_0+T_{pred}$] to come. At the end of this step, processing and control unit 105 may further program injection device 103 to administer the doses determined during the prediction period [t0, $t_0+T_{pred}$] to come.

Steps 403 of prediction of the blood glucose and 405 of determination of the future doses of insulin to be administered may for example be repeated for each update of the physiological model (that is, after each iteration of step 401), for each new carbohydrate ingestion notified by the patient, for each new administration of an insulin dose by injection device 103, and/or each time a significant physical activity of the patient is detected.

An advantage of the system described in relation with FIGS. 5, 6, and 7 is that it enables to make blood glucose predictions more reliable than systems based on physiological models which do not take into account the patient's physical activity, particularly during and around periods of physical activity.

Specific embodiments have been described. Various alterations and modifications will occur to those skilled in the art. In particular, the described embodiments are not limited to the described examples of use of the blood glucose prediction system of FIG. 5. More generally, the provided prediction system, based on the use of a physiological model taking into account the patient's physical activity, may be used for any application capable of taking advantage of a reliable prediction of the future trend of a patient's blood glucose.

Further, the described embodiments are not limited to the above-described example where the input variable EE(t) of the model is calculated by taking into account an output signal of a sensor of the patient's motions and an output signal of a sensor of the patient's heart rate. As a variant, input variable EE(t) may be calculated by taking into account the output signal of the motion sensor only or the output signal of the heart rate sensor only. More generally, input variable EE(t) may be formed by any signal or combination of signals representative of the patient's physical activity. As an example, input variable EE(t) may be a combination of a signal measured by means of any sensor, for example, the motion sensor 505 and/or the heart rate sensor 507 of FIG. 5, and of a signal of physical activity intensity declared by the patient by means of a user interface (not detailed). As a variant, input variable EE(t) may be calculated only from a signal of activity intensity declared by the patient.

Further, the described embodiments are not limited to the specific case described in relation with FIG. 7 where the physiological model is an adaptation of the Hovorka model. More generally, the described embodiments are compatible with any other physiological model describing the assimilation of insulin by a patient's body and its effect on the patient's blood glucose, and taking into account the patient's energy expenditure and, more particularly, a glucose consumption by the muscles due to the patient's energy expenditure (the above-described term $-(K_{EE}*EE(t))$).

The invention claimed is:

1. An automated system for controlling a patient's blood glucose, comprising a processing and control unit configured to predict the future trend of the patient's blood glucose based on a physiological model, wherein the physiological model comprises a differential equation system describing the time variation of a plurality of state variables, and wherein at least one of the equations of the system takes as an input a variable EE(t) representative of the time variation of the patient's energy expenditure, wherein said at least one equation is defined as follows:

$$\frac{dQ_2}{dt} = x_1(t) \cdot Q_1(t) - [k_{12} + x_2(t)] \cdot Q_2(t) - k_{EE} \cdot EE(t) \quad 5$$

where $Q_1$ and $Q_2$ are state variables respectively corresponding to glucose masses in first and second compartments, where $x_1$ and $x_2$ are state variables, each standing for an action of insulin on the kinetics of glucose, where $k_{12}$ and $K_{EE}$ are parameters of the physiological model, term $-(K_{EE}*EE(t))$ being representative of a glucose consumption by the muscles;

further comprising a device for measuring a physical activity of the patient, the input variable EE(t) of the model being calculated by the processing and control unit based on the output data PA (t) of the measurement device;

further comprising a blood glucose sensor; and further comprising an insulin injection device, wherein the processing and control unit is capable of controlling the insulin injection device, taking into account the prediction of the future trend of the patient's blood glucose made based on the physiological model, wherein $k_{EE}$ is a constant or time-dependent parameter of the physiological model, and wherein EE(t) is based on heart rate data from the patient during exercise and at rest and on a signal representative of motions performed by the patient.

2. System according to claim 1, wherein the measurement device comprises a sensor of the patient's motions.

3. System according to claim 2, wherein the measurement device further comprises a sensor of the patient's heart rate.

4. System according to claim 3, wherein the motion sensor delivers a signal $S_{CPM}$ representative of motions performed by the patient, and the heart rate sensor delivers a signal $S_{HR}$ representative of the patient's heart rate, and wherein the input variable EE(t) of the model is calculated as follows by the processing and control unit:

$$EE(t) = \begin{cases} \alpha_1 * S_{HR}(t) + \beta_1, & S_{HR} \geq S1 \\ \alpha_2 * S_{LC}(t) + \beta_2, & S_{HR} < S1 \text{ et } S_{LC} < S2 \\ \alpha_3 * S_{LC}(t) + \beta_3, & S_{HR} < S1 \text{ et } S_{LC} \geq S2 \end{cases}$$

where signal $S_{LC}$ is a linear combination of signals $S_{HR}$ and $S_{CMP}$, and where quantities $\alpha_1, \alpha_2, \alpha_3, \beta_1, \beta_2, \beta_3$, S1, and S2 are parameters of the system.

5. System according to claim 1, wherein the physiological model further takes as inputs a variable i(t) representative of the time variation of the quantity of insulin injected to the patient, and a variable cho(t) representative of the time variation of the quantity of carbohydrates ingested by the patient.

6. System according to claim 5, wherein the processing and control unit is capable of implementing a step of automatic calibration of the physiological model comprising a step of estimation of a set of parameters of the differential equation system by minimization of a quantity m representative of the error, during a past observation period, between the blood glucose estimated based on the physiological model and the blood glucose measured by the sensor.

7. System according to claim 6, wherein said quantity is defined as follows:

$$m = \frac{1}{\Delta T} \sum_{t=t_0}^{t_0+\Delta T} |G^r(t) - G(t)|^2$$

where t is a discretized time variable, $t_0$ is the time of beginning of the past observation period, and $t_0+\Delta T$ is the time of end of the past observation period.

* * * * *